(12) United States Patent
Boutelet et al.

(10) Patent No.: US 6,955,803 B2
(45) Date of Patent: *Oct. 18, 2005

(54) PHOTOPROTECTIVE COMPOSITIONS COMPRISING SULFONIC/HYDROPHOBIC AMPHIPHILIC POLYMERS

(75) Inventors: Karl Boutelet, Paris (FR); Didier Candau, Bievres (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/616,947

(22) Filed: Jul. 11, 2003

(65) Prior Publication Data

US 2004/0062728 A1 Apr. 1, 2004

Related U.S. Application Data

(63) Continuation of application No. PCT/FR02/00030, filed on Jan. 4, 2002.

(30) Foreign Application Priority Data

Jan. 11, 2001 (FR) .............................. 01 00334

(51) Int. Cl.⁷ .............................. A61K 7/42; A61K 7/44; A61K 31/74; A61K 7/00
(52) U.S. Cl. .................. 424/59; 424/60; 424/78.02; 424/78.08; 424/400; 424/401
(58) Field of Search .................. 424/59, 60, 78.02, 424/78.08, 400, 401

(56) References Cited

U.S. PATENT DOCUMENTS

| 4,460,732 A | 7/1984 | Buscall et al. |
| 4,861,499 A | 8/1989 | Neff et al. |
| 5,089,578 A | 2/1992 | Valint et al. |
| 5,114,706 A | 5/1992 | Duvel |
| 5,318,995 A | 6/1994 | Mondet et al. |
| 5,464,452 A | 11/1995 | Cole et al. |
| 6,287,543 B1 | 9/2001 | Terren et al. |
| 6,465,402 B1 | 10/2002 | Lorant |
| 6,645,476 B1 | 11/2003 | Morschhäuser et al. |
| 2004/0109835 A1 | 6/2004 | Loffler et al. |

FOREIGN PATENT DOCUMENTS

| EP | 0 406 042 A2 | 1/1991 |
| EP | 0 750 899 A2 | 1/1997 |
| EP | 0 815 843 A1 | 1/1998 |
| EP | 1 069 142 A1 | 1/2001 |
| EP | 1 055 406 A2 | 11/2002 |
| WO | 0 945 124 A2 | 9/1999 |
| WO | 00/25731 A1 | 5/2000 |
| WO | 00/31154 A1 | 6/2000 |
| WO | 00/57893 A1 | 10/2000 |
| WO | 02/43689 | 6/2002 |

OTHER PUBLICATIONS

Kobayashi et al., *Journal of Applied Polymer Science*, vol. 73, No. 12, Sep. 19, 1999, pp. 2447–2453, John Wiley and Sons, Inc., New York.

Patent Abstracts of Japan, vol. 1997, No. 2, Feb. 28, 1997, abstract of JP 08 252447A published Oct. 1, 1996.

Primary Examiner—Shelley A. Dodson
(74) Attorney, Agent, or Firm—Buchanan Ingersoll, P.C.; Burns, Doane, Swecker & Mathis

(57) ABSTRACT

Photoprotective cosmetic/dermatological compositions well suited for the UV-photoprotection of human skin and/or hair, comprise (a) at least one organic UV-screening agent and (b) an SPF-improving amount of at least one amphiphilic polymerizate of at least one ethylenically unsaturated monomer which comprises a sulfonic group, whether in the free acid or in partially or totally neutralized state, and which amphiphilic polymerizate also comprises at least one hydrophobic moiety.

54 Claims, No Drawings

PHOTOPROTECTIVE COMPOSITIONS COMPRISING SULFONIC/HYDROPHOBIC AMPHIPHILIC POLYMERS

CROSS-REFERENCE TO PRIORITY/PCT APPLICATIONS

This application claims priority under 35 U.S.C. § 119 of FR-01/00334, filed Jan. 11, 2001, and is a continuation of PCT/FR02/00030, filed Jan. 4, 2002 and designating the United States (published in the French language on Jul. 18, 2002 as WO 02/055037 A1; the title and abstract were also published in English), both hereby expressly incorporated by reference.

CROSS-REFERENCE TO COMPANION APPLICATION

Our copending application Ser. No. 10/617092, filed concurrently herewith and assigned to the assignee thereof.

BACKGROUND OF THE INVENTION

1. Technical Field of the Invention

The invention relates to cosmetic compositions for topical use, in particular for photoprotection of the skin and/or the hair, which comprise, in a cosmetically acceptable support, (a) at least one organic UV-screening agent and (b) at least one amphiphilic polymer comprising at least one ethylenically unsaturated monomer containing a sulfonic group, in free form or partially or totally neutralized form, and comprising at least one hydrophobic portion or moiety. The invention also relates to the use of these compositions for protecting the skin and the hair against the effects of ultraviolet radiation.

2. Description of Background/Related/Prior Art

It is known that light radiation with wavelengths of between 280 nm and 400 nm permit tanning of the human epidermis, and that light rays with wavelengths more particularly between 280 nm and 320 nm, which are known as UV-B rays, cause skin burns and erythema that may harm the development of a natural tan. For these reasons, and also for aesthetic reasons, there is a constant demand for means for controlling this natural tanning in order thus to control the color of the skin; this UV-B radiation should thus be screened out.

It is also known that UV-A rays, with wavelengths of between 320 nm and 400 nm, which cause tanning of the skin, are liable to induce an impairment thereof, especially in the case of sensitive skin or of skin that is continually exposed to sunlight. In particular, UV-A rays cause a loss of elasticity of the skin and the appearance of wrinkles, leading to premature aging of the skin. They promote the triggering of the erythemal reaction or amplify this reaction in certain individuals and may even be the cause of phototoxic or photoallergic reactions. Thus, for aesthetic and cosmetic reasons, for instance preserving the natural elasticity of the skin, more and more individuals wish to control the effect of UV-A rays on their skin. It is thus desirable also to screen out UV-A radiation.

Many cosmetic compositions intended for photoprotection (against UV-A and/or UV-B) of the skin have been proposed to date.

These antisun compositions are quite often in the form of an emulsion, of oil-in-water type (i.e., a cosmetically and/or dermatologically acceptable support consisting of an aqueous dispersing continuous phase and a fatty dispersed discontinuous phase) or water-in-oil type (aqueous phase dispersed in a continuous fatty phase), which contains, in varying concentrations, one or more standard liposoluble organic screening agents and/or standard organic water-soluble screening agents, capable of selectively absorbing the harmful UV radiation, these screening agents (and the amounts thereof) being selected as a function of the desired sun protection factor, the sun protection factor (SPF) mathematically expressing the ratio of the dose of UV radiation required to reach the erythema-forming threshold with the UV-screening agent to the dose of UV radiation required to reach the erythema-forming threshold without a UV-screening agent. In such emulsions, the hydrophilic screening agents are present in the aqueous phase and the lipophilic screening agents are present in the fatty phase.

Users generally prefer oil-in-water emulsions to water-in-oil emulsions, especially on account of their pleasant feel (close to water) and their presentation in the form of a milk or a non-greasy cream; however, they also more readily lose their anti-UV efficacy once they come into contact with water; the reason for this is that water-soluble screening agents have a tendency to be lost in water, on bathing in the sea or in a swimming pool, under the shower or when practicing water sports; thus, the antisun compositions they contain, alone or combined with lipophilic screening agents, no longer provide the desired initial protection once the substrate (skin or hair) onto which they have been applied comes into contact with water.

It is possible to obtain antisun compositions with improved water resistance by using water-in-oil emulsions. The reason for this is that a hydrophilic screening agent is more water-resistant in a water-in-oil emulsion than in an oil-in-water emulsion. However, as has been mentioned above, such compositions are still not entirely satisfactory since, after they have been applied, they leave a greasy impression that users find particularly unpleasant.

Thus, there is still a need to be able to obtain antisun compositions that give the skin and/or the hair effective antisun protection, which is stable over time and water-resistant, and the cosmetic performance qualities of which are comparable to those obtained with standard oil/water emulsions.

SUMMARY OF THE INVENTION

It has now surprisingly and unexpectedly been determined that particular compositions containing at least one organic UV-screening agent and at least one amphiphilic polymer comprising at least one ethylenically unsaturated monomer containing a sulfonic group, in free form or partially or totally neutralized form and comprising at least one hydrophobic portion, not only make it possible to formulate antisun compositions whose cosmetic performance qualities are comparable with those generally obtained with a standard antisun composition in oil/water emulsion form, but also show an improved sun protection factor (SPF) and also good water resistance.

These discoveries form the basis of the present invention.

Thus, in accordance with one of the subjects of the present invention, novel cosmetic compositions are now proposed, in particular for photoprotection of the skin and/or the hair, comprising, in a cosmetically acceptable support: (a) at least one organic UV-screening agent and (b) at least one amphiphilic polymer comprising at least one ethylenically unsaturated monomer containing a sulfonic group, in free form or partially or totally neutralized form, and comprising at least one hydrophobic portion or moiety.

A subject of the present invention is also the use of such compositions for manufacturing cosmetics intended to protect the skin and/or the hair against ultraviolet radiation and in particular sunlight.

Another subject of the present invention is the use of an amphiphilic polymer containing at least one ethylenically unsaturated monomer containing a sulfonic group, in free form or partially or totally neutralized form, and comprising at least one hydrophobic portion in a photoprotective cosmetic or dermatological composition comprising at least one organic UV-screening agent, for the purpose of increasing its sun protection factor (SPF) and/or its water resistance. The invention also relates to this composition for manufacturing cosmetic compositions for protecting the skin and/or the hair against ultraviolet radiation, in particular solar radiation.

Other characteristics, aspects and advantages of the present invention will become apparent on reading the detailed description that follows.

DETAILED DESCRIPTION OF BEST MODE AND SPECIFIC/PREFERRED EMBODIMENTS OF THE INVENTION

The polymers in accordance with the invention are amphiphilic polymers comprising at least one ethylenically unsaturated monomer containing a sulfonic group, in free form or partially or totally neutralized form, and comprising at least one hydrophobic portion.

The expression "amphiphilic polymer" means any polymer comprising both a hydrophilic portion and a hydrophobic portion and especially a fatty chain.

The hydrophobic portion present in the polymers of the invention preferably contains from 6 to 50 carbon atoms, more preferably from 6 to 22 carbon atoms, even more preferably from 6 to 18 carbon atoms and more particularly from 12 to 18 carbon atoms.

Preferably, the polymers in accordance with the invention are partially or totally neutralized with a mineral base (sodium hydroxide, potassium hydroxide or aqueous ammonia) or an organic base such as mono-, di- or triethanolamine, an aminomethylpropanediol, N-methylglucamine, basic amino acids, for instance arginine and lysine, and mixtures of these compounds.

The amphiphilic polymers in accordance with the invention generally have a number-average molecular weight ranging from 1,000 to 20,000,000 g/mol, preferably ranging from 20,000 to 5,000,000 and even more preferably from 100,000 to 1,500,000 g/mol.

The amphiphilic polymers according to the invention may or may not be crosslinked. Crosslinked amphiphilic polymers are preferably chosen. When they are crosslinked, the crosslinking agents may be chosen from polyolefinically unsaturated compounds commonly used for the crosslinking of polymers obtained by free-radical polymerization.

Mention may be made, for example, of divinylbenzene, diallyl ether, dipropylene glycol diallyl ether, polyglycol diallyl ethers, triethylene glycol divinyl ether, hydroquinone diallyl ether, ethylene glycol di(meth)acrylate or tetraethylene glycol di(meth)-acrylate, trimethylolpropane triacrylate, methylenebis-acrylamide, methylenebismethacrylamide, triallylamine, triallyl cyanurate, diallyl maleate, tetraallylethylenediamine, tetraallyloxyethane, trimethylol-propane diallyl ether, allyl (meth)acrylate, allylic ethers of alcohols of the sugar series, or other allyl or vinyl ethers of polyfunctional alcohols, and also allylic esters of phosphoric and/or vinylphosphonic acid derivatives, or mixtures of these compounds.

Methylenebisacrylamide, allyl methacrylate or trimethylolpropane triacrylate (TMPTA) will be used more particularly. The degree of crosslinking will generally range from 0.01 mol % to mol % and more particularly from 0.2 mol % to 2 mol % relative to the polymer.

The ethylenically unsaturated monomers containing a sulfonic group are chosen especially from vinylsulfonic acid, styrenesulfonic acid, (meth)acrylamido($C_1$–$C_{22}$) alkylsulfonic acids, and N-($C_1$–$C_{22}$)alkyl(meth)acrylamido ($C_1$–$C_{22}$)alkylsulfonic acids, for instance undecylacrylamidomethanesulfonic acid, and also partially or totally neutralized forms thereof.

(Meth)acrylamido($C_1$–$C_{22}$)alkylsulfonic acids such as, for example, acrylamidomethanesulfonic acid, acrylamidoethanesulfonic acid, acrylamidopropane-sulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylami- dododecylsulfonic acid or 2-acrylamido-2,6-dimethyl-3-heptanesulfonic acid, and also partially or totally neutralized forms thereof, will more preferably be used.

2-Acrylamido-2-methylpropanesulfonic acid (AMPS), and also partially or totally neutralized forms thereof, will more particularly be used.

The amphiphilic polymers in accordance with the invention may be chosen especially from random amphiphilic AMPS polymers modified by reaction with a $C_6$–$C_{22}$ n-monoalkylamine or di-n-alkylamine, and such as those described in WO 00/31154 (forming an integral part of the content of the description). These polymers may also contain other ethylenically unsaturated hydrophilic monomers chosen, for example, from (meth)acrylic acids, β-substituted alkyl derivatives thereof or esters thereof obtained with monoalcohols or mono- or polyalkylene glycols, (meth) acrylamides, vinylpyrrolidone, maleic anhydride, itaconic acid or maleic acid, or mixtures of these compounds.

The preferred polymers of the invention are chosen from amphiphilic copolymers of AMPS and of at least one ethylenically unsaturated hydrophobic monomer comprising at least one hydrophobic portion containing from 6 to 50 carbon atoms, more preferably from 6 to 22 carbon atoms, even more preferably from 6 to 18 carbon atoms and more particularly 12 to 18 carbon atoms. These same copolymers may also contain one or more ethylenically unsaturated monomers not comprising a fatty chain, such as (meth) acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described especially in EP-A-750 899, U.S. Pat. No. 5,089,578 and in the following publications from Yotaro Morishima:

"Self-assembling amphiphilic polyelectrolytes and their nanostructures—Chinese Journal of Polymer Science Vol. 18, No. 40, (2000), 323–336";

"Micelle formation of random copolymers of sodium 2-(acrylamido)-2-methylpropanesulfonate and a nonionic surfactant macromonomer in water as studied by fluorescence and dynamic light scattering—Macromolecules 2000, Vol. 33, No. 10-3694–3704";

"Solution properties of micelle networks formed by nonionic moieties covalently bound to a polyelectrolyte: salt effects on rheological behaviour—Langmuir, 2000, Vol. 16, No. 12, 5324–5332";

"Stimuli responsive amphiphilic copolymers of sodium 2-(acrylamido)-2-methylpropanesulfonate and associative macromonomers—Polym. Preprint, Div. Polym. Chem. 1999, 40(2), 220–221".

The ethylenically unsaturated hydrophobic monomers of these particular copolymers are preferably chosen from the acrylates or acrylamides of formula (I) below:

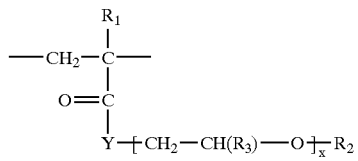
(I)

in which $R_1$ and $R_3$, which may be identical or different, denote a hydrogen atom or a linear or branched $C_1$–$C_6$ alkyl radical (preferably methyl); Y denotes O or NH; $R_2$ denotes a hydrophobic hydrocarbon-based radical containing at least from 6 to 50 carbon atoms, more preferably from 6 to 22 carbon atoms, even more preferably from 6 to 18 carbon atoms and more particularly from 12 to 18 carbon atoms; x denotes a number of moles of alkylene oxide and ranges from 0 to 100.

The radical $R_2$ is preferably chosen from linear $C_6$–$C_{18}$ alkyl radicals (for example n-hexyl, n-octyl, n-decyl, n-hexadecyl and n-dodecyl) and branched or cyclic $C_6$–$C_{18}$ alkyl radicals (for example cyclododecane ($C_{12}$) or adamantane ($C_{10}$)); $C_6$–$C_{18}$ alkyl-perfluoro radicals (for example the group of formula —$(CH_2)_2$—$(CF_2)_9$—$CF_3$); the cholesteryl radical ($C_{27}$) or a cholesterol ester residue, for instance the cholesteryl oxyhexanoate group; aromatic polycyclic groups, for instance naphthalene or pyrene.

Among these radicals, the ones that are more particularly preferred are linear alkyl radicals and more particularly the n-dodecyl radical. According to one particularly preferred form of the invention, the monomer of formula (I) comprises at least one alkylene oxide unit ($x \geq 1$) and preferably a polyoxyalkylenated chain. The polyoxyalkylenated chain preferably consists of ethylene oxide units and/or of propylene oxide units and even more particularly consists of ethylene oxide units. The number of oxyalkylene units generally ranges from 3 to 100, more preferably from 3 to 50 and even more preferably from 7 to 25.

Among these polymers, mention may be made of:

crosslinked or non-crosslinked, neutralized or non-neutralized copolymers comprising from 15% to 60% by weight of AMPS units and from 40% to 85% by weight of ($C_8$–$C_{16}$)alkyl(meth)acrylamide units or of ($C_8$–$C_{16}$)alkyl (meth)acrylate units, relative to the polymer, such as those described in EP-A-750,899;

terpolymers comprising from 10 mol % to 90 mol % of acrylamide units, from 0.1 mol % to 10 mol % of AMPS units and from 5 mol % to 80 mol % of n-($C_6$–$C_{18}$)alkyl-acrylamide units, such as those described in U.S. Pat. No. 5,089,578.

Mention may also be made of copolymers of totally neutralized AMPS and of dodecyl methacrylate, and also crosslinked and non-crosslinked copolymers of AMPS and of n-dodecylmethacrylamide, such as those described in the Morishima articles mentioned above.

Mention will be made more particularly of the copolymers consisting of 2-acrylamido-2-methylpropane-sulfonic acid (AMPS) units of formula (II) below:

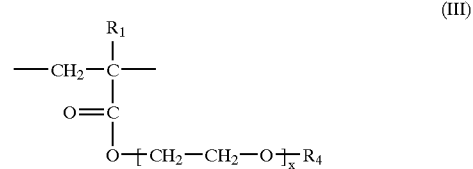
(II)

in which $X^+$ is a proton, an alkali metal cation, an alkaline-earth metal cation or the ammonium ion, and of units of formula (III) below:

(III)

in which x denotes an integer ranging from 3 to 100, preferably from 5 to 80 and more preferably from 7 to 25; $R_1$ has the same meaning as that given above in formula (I) and $R_4$ denotes a linear or branched $C_6$–$C_{22}$ and more preferably $C_{10}$–$C_{22}$ alkyl.

The polymers that are particularly preferred are those for which x=25, $R_1$ denotes methyl and $R_4$ represents n-dodecyl; they are described in the Morishima articles mentioned above. The polymers for which $X^+$ denotes sodium or ammonium are more particularly preferred.

The preferred amphiphilic polymers in accordance with the invention may be obtained according to the standard free-radical polymerization processes in the presence of one or more initiators such as, for example, azobisisobutyronitrile (AIBN), azobisdimethyl-valeronitrile, ABAH (2,2-azobis[2-amidinopropane]hydrochloride), organic peroxides such as diluaryl peroxide, benzoyl peroxide, tert-butyl hydroperoxide, etc., mineral peroxide compounds such as potassium persulfate or ammonium persulfate, or $H_2O_2$ optionally in the presence of reducing agents.

The amphiphilic polymers are obtained especially by free-radical polymerization in tert-butanol medium in which they precipitate.

Using precipitation polymerization in tert-butanol, it is possible to obtain a size distribution of the polymer particles that is particularly favorable for its uses.

The size distribution of the polymer particles may be determined, for example, by laser diffraction or image analysis.

An advantageous distribution for this type of polymer, determined by image analysis, is as follows: 60.2% less than 423 microns, 52.0% less than 212 microns, 26.6% less than 106 microns, 2.6% less than 45 microns and 26.6% greater than 850 microns.

The reaction may be performed at a temperature of between 0 and 150° C., preferably between 10 and 100° C., either at atmospheric pressure or under reduced pressure. It may also be performed under inert atmosphere, and preferably under nitrogen. According to this process 2-acrylamido-2-methylpropane-sulfonic acid (AMPS) or a sodium or ammonium salt thereof was especially polymerized with a (meth)acrylic acid ester and a $C_{10}$–$C_{18}$ alcohol oxyethylenated with 8 mol of ethylene oxide (Genapol® C-080 from Hoechst/Clariant), a $C_{11}$ oxo alcohol oxyethylenated with 8 mol of ethylene oxide (Genapol® UD-080 from Hoechst/Clariant), a $C_{11}$ oxo alcohol oxyethylenated with 7 mol of ethylene oxide (Genapol® UD-070 from Hoechst/Clariant), a $C_{12}$–$C_{14}$ alcohol oxyethylenated with 7 mol of ethylene oxide (Genapol® LA-070 from Hoechst/Clariant), a $C_{12}$–$C_{14}$ alcohol oxyethylenated with 9 mol of ethylene oxide (Genapol® LA-090 from Hoechst/Clariant), a $C_{12}$–$C_{14}$ alcohol oxyethylenated with 11 mol of ethylene oxide (Genapol® LA-110 from Hoechst/Clariant), a $C_{16}$–$C_{18}$ alcohol oxyethylenated with 8 mol of ethylene oxide (Genapol® T-080 from Hoechst/Clariant), a $C_{16}$–$C_{18}$ alcohol oxyethylenated with 15 mol of ethylene oxide (Genapol® T-150 from Hoechst/Clariant), a $C_{16}$–$C_{18}$ alcohol oxyethylenated with 11 mol of ethylene oxide (Genapol® T-110 from Hoechst/Clariant), a $C_{16}$–$C_{18}$ alcohol oxyethylenated with 20 mol of ethylene oxide (Genapol® T-200 from Hoechst/Clariant), a $C_{16}$–$C_{18}$ alcohol oxyethylenated with 25 mol of ethylene oxide (Genapol® T-250 from Hoechst/Clariant), a $C_{18}$–$C_{22}$ alcohol oxyethylenated with 25 mol of ethylene oxide and/or a $C_{16}$–$C_{18}$ iso alcohol oxyethylenated with 25 mol of ethylene oxide.

The molar % concentration of the units of formula (II) and of the units of formula (III) in the polymers according to the invention will vary as a function of the desired cosmetic use and of the desired rheological properties of the formulation. It may range between 0.1 mol % and 99.9 mol %.

Preferably, for the most hydrophobic polymers, the molar proportion of units of formula (I) or (III) ranges from 50.1% to 99.9%, more particularly from 70% to 95% and even more particularly from 80% to 90%.

Preferably, for the sparingly hydrophobic polymers, the molar proportion of units of formula (I) or (III) ranges from 0.1% to 50%, more particularly from 5% to 25% and even more particularly from 10% to 20%.

The monomer distribution in the polymers of the invention may be, for example, alternating, block (including multiblock) or random.

According to the invention, it is preferable for the polymers to contain heat-sensitive pendant chains and for the aqueous solution thereof to have a viscosity that, beyond a certain threshold temperature, increases or remains virtually constant as the temperature increases.

Even more particularly, the preferred polymers are those whose aqueous solution has a viscosity that is low below a first threshold temperature and that, above this first threshold temperature, increases to a maximum as the temperature increases, and that, above a second threshold temperature, decreases again as the temperature increases. From this perspective, it is preferable for the viscosity of the polymer solutions below the first threshold temperature to be from 5% to 50%, in particular from 10% to 30% of the maximum viscosity at the second threshold temperature. These polymers preferably lead in water to a phenomenon of demixing by heating, reflected by curves showing, as a function of the temperature and the concentration, a minimum known as the LCST (Lower Critical Solution Temperature).

The viscosities (measured at 25° C. using a Brookfield viscometer, needle No. 7) of the aqueous 1% solutions preferably range from 20,000 mPa·s to 100,000 mPa·s and more particularly from 60,000 mPa·s to 70,000 mPa·s.

The amphiphilic polymers in accordance with the invention are present in the compositions in concentrations ranging from 0.01% to 30% by weight, more preferably from 0.1% to 10%, even more preferably from 0.1% to 5% by weight and even more particularly from 0.5% to 2% by weight.

The amphiphilic polymers used according to the invention may, for example, be prepared as follows:

Preparation of the Ethoxylated (Meth)Acrylic Esters:

These may be obtained especially by the action of glycidyl (meth)acrylate or of (meth)acrylic acid, or of an alkyl (meth)acrylate, or of a (meth)acryloyl halide on an ethoxylated fatty alcohol. Non-limiting examples that may be mentioned include the following preparations:

a) from glycidyl methacrylate and Genapol T-250 b) from (meth)acrylic acid and Genapol UD-070 c) from methyl (meth)acrylate and Genapol LA-090 d) from (meth)acryloyl chloride and Genapol UD-070.

a) 500 g of Genapol T-250 and 75 g of glycidyl methacrylate are placed in a one-liter three-necked reactor equipped with a stirrer, a thermometer and a reflux condenser. The reaction mixture is heated at a temperature of 100° C. for 2 hours and the excess glycidyl methacrylate is removed by distillation under reduced pressure. The monomer obtained may be used for polymerization without further purification.

b) 500 g of Genapol UD-070, 100 g of (meth)acrylic acid and p-toluenesulfonic acid as catalyst are placed in a one-liter three-necked reactor equipped with a stirrer, a thermometer and a reflux condenser. The reaction mixture is refluxed for 2 hours and the excess acid and water formed during the reaction are separated out by distillation under reduced pressure. The monomer obtained may be used for polymerization without further purification.

c) 500 g of Genapol LA-090, 100 g of methyl (meth) acrylate and 20 g of titanium tetraisopropoxide are placed in a one-liter three-necked reactor equipped with a stirrer, a thermometer and a reflux condenser. The reaction mixture is refluxed for 2 hours and, after separating out the alcohol formed by distillation, the remaining ester is distilled under reduced pressure.

The monomer obtained may be used for polymerization without further purification.

d) 500 g of Genapol UD-070, 110 g of (meth)acryloyl chloride and 50 g of sodium carbonate are placed in a one-liter three-necked reactor equipped with a stirrer, a thermometer and a reflux condenser. The reaction mixture is refluxed for 2 hours and the excess acid chloride is separated out by distillation under reduced pressure. The monomer obtained may be used for polymerization without further purification.

Polymerization According to the Precipitation Method in Tert-butanol:

500 ml of tert-butanol and the calculated amount of AMPS are placed in a 2-liter reactor equipped with a reflux condenser, a gas inlet, a thermometer and a stirrer. The mixture is neutralized by introducing $NH_3$, and the monomer prepared above is added to the reaction mixture. The reaction mixture is made inert by passing nitrogen or argon there through and, when the internal temperature has reached 60° C., the initiator (AIBN) is introduced to initiate the polymerization.

After a few minutes, the polymer thus prepared precipitates. The mixture is refluxed for 2 hours and the polymer is separated from the solvent by vacuum filtration and is then dried under reduced pressure.

The polymers below were prepared in the manner described above: (from the following reagents in amounts expressed in grams)

|  | Polymer P1 | Polymer P2 | Polymer P3 | Polymer P4 |
|---|---|---|---|---|
| Genapol T-250 methacrylate | 10 | 20 | 30 | 97 |
| AMPS neutralized with $NH_3$ | 90 | 80 | 90 | 3 |
| Methylenebisacrylamide (crosslinking agent) |  |  | 1.5 |  |
| Allyl methacrylate (crosslinking agent) |  | 1.7 |  |  |
| TMPTA (crosslinking agent) | 1.8 |  |  | 1.8 |
| Azobisisobutyronitrile (initiator) |  |  | 1 |  |
| Dilauryl peroxide (initiator) | 1 | 1 |  | 1 |
| Tert-Butanol | 300 | 300 | 300 | 300 |

Polymers P1 and P2 are used in the examples.

The organic UV-screening agents according to the invention are chosen especially from anthranilates; cinnamic derivatives; dibenzoylmethane derivatives; salicylic derivatives; camphor derivatives; triazine derivatives such as those described in U.S. Pat. No. 4,367,390, EP-863,145, EP-517,104, EP-570,838, EP-796,851, EP-775,698, EP-878,469 and EP-933,376; benzophenone derivatives; β,β'-diphenylacrylate derivatives; benzotriazole derivatives; benzimidazole derivatives; imidazolines; bis-benzazolyl derivatives as described in EP-669,323 and U.S. Pat. No. 2,463,264; p-aminobenzoic acid (PABA) derivatives; methylenebis(hydroxyphenylbenzotriazole) derivatives such as those described in U.S. Pat. Nos. 5,237,071, 6,166,355, GB-2-303,549, DE-197,26,184 and EP-893,119; screening polymers and screening silicones such as those described especially in WO 93/04665; dimers derived from α-alkylstyrene, such as those described in DE-198,55,649.

As examples of additional UV-A-active and/or UV-B-active organic screening agents, mention may be made of the following, denoted herein below under their INCI name:

Para-aminobenzoic Acid Derivatives:
   PABA,
   Ethyl PABA,
   Ethyl dihydroxypropyl PABA,
   Ethylhexyl dimethyl PABA sold in particular under the name "Escalol 507" by ISP,
   Glyceryl PABA,
   PEG-25 PABA sold under the name "Uvinul P25" by BASF.

Salicylic Derivatives:
   Homosalate sold under the name "Eusolex HMS" by Rona/EM Industries,
   Ethylhexyl salicylate sold under the name "Neo Heliopan OS" by Haarmann and Reimer,
   Dipropylene glycol salicylate sold under the name "Dipsal" by Scher,
   TEA salicylate sold under the name "Neo Heliopan TS" by Haarmann and Reimer.

Dibenzoylmethane Derivatives:
   Butyl methoxydibenzoylmethane sold in particular under the trademark "Parsol 1789" by Hoffmann LaRoche,
   Isopropyldibenzoylmethane.

Cinnamic Derivatives:
   Ethylhexyl methoxycinnamate sold in particular under the trademark "Parsol MCX" by Hoffmann LaRoche,
   Isopropyl methoxycinnamate,
   Isoamyl methoxycinnamate sold under the trademark "Neo Heliopan E 1000" by Haarmann and Reimer,
   Cinoxate,
   DEA methoxycinnamate,
   Diisopropyl methoxycinnamate,
   Glyceryl ethylhexanoate dimethoxycinnamate.

β,β'-Diphenylacrylate Derivatives:
   Octocrylene sold in particular under the trademark "Uvinul N539" by BASF,
   Etocrylene sold in particular under the trademark "Uvinul N35" by BASF.

Benzophenone Derivatives:
   Benzophenone-1 sold under the trademark "Uvinul 400" by BASF,
   Benzophenone-2 sold under the trademark "Uvinul D50" by BASF,
   Benzophenone-3 or Oxybenzone sold under the trademark "Uvinul M40" by BASF,
   Benzophenone-4 sold under the trademark "Uvinul MS40" by BASF,
   Benzophenone-5,
   Benzophenone-6 sold under the trademark "Helisorb 11" by Norquay,
   Benzophenone-8 sold under the trademark "Spectra-Sorb UV-24" by American Cyanamid,
   Benzophenone-9 sold under the trademark "Uvinul DS-49" by BASF,
   Benzophenone-12.

Benzylidenecamphor Derivatives:
   3-Benzylidenecamphor manufactured under the name "Mexoryl SD" by Chimex,
   4-Methylbenzylidenecamphor sold under the name "Eusolex 6300" by Merck,
   Benzylidenecamphorsulfonic acid manufactured under the name "Mexoryl SL" by Chimex,
   Camphor benzalkonium methosulfate manufactured under the name "Mexoryl SO" by Chimex,
   Terephthalylidenedicamphorsulfonic acid manufactured under the name "Mexoryl SX" by Chimex,
   Polyacrylamidomethylbenzylidenecamphor manufactured under the name "Mexoryl SW" by Chimex.

Phenylbenzimidazole Derivatives:
   Phenylbenzimidazolesulfonic acid sold in particular under the trademark "Eusolex 232" by Merck,
   Benzimidazilate, sold under the trade trademark "Neo Heliopan AP" by Haarmann and Reimer.

Triazine Derivatives:
   Anisotriazine sold under the trademark "Tinosorb S" by Ciba Geigy,
   Ethylhexyltriazone sold in particular under the trademark "Uvinul T150" by BASF,
   Diethylhexylbutamidotriazone sold under the trademark "Uvasorb HEB" by Sigma 3V.

Phenylbenzotriazole Derivatives:
   Drometrizole trisiloxane sold under the name "Silatrizole" by Rhodia Chimie,
   Methylenebis(benzotriazolyl)tetramethylbutylphenol sold in solid form under the trademark "MIXXIM BB/100" by Fairmount Chemical or in micronized form in aqueous dispersion under the trademark "Tinosorb M" by Ciba Specialty Chemicals.

Anthranilic Derivatives:
   Menthyl anthranilate sold under the trade trademark "Neo Heliopan MA" by Haarmann and Reimer.

Imidazoline Derivatives:
   Ethylhexyldimethoxybenzylidenedioxoimidazoline propionate.

Benzalmonate Derivatives:
   Polyorganosiloxane containing benzalmalonate functions, sold under the trademark "Parsol SLX" by Hoffmann LaRoche, and mixtures thereof.

The organic UV-screening agents that are more particularly preferred are chosen from the following compounds:
   ethylhexyl salicylate,
   butylmethoxydibenzoylmethane,
   ethylhexyl methoxycinnamate,
   octocrylene,
   phenylbenzimidazolesulfonic acid,
   terephthalylidenedicamphorsulfonic,
   benzophenone-3,
   benzophenone-4,
   benzophenone-5,
   4-methylbenzylidenecamphor,
   benzimidazilate,
   anisotriazine,
   ethylhexyltriazone,
   diethylhexylbutamidotriazone,
   methylenebis(benzotriazolyl)tetramethylbutyl-phenol,
   drometrizole trisiloxane, and mixtures thereof.

The organic UV-screening agents are generally present in the compositions according to the invention in proportions ranging from 0.1% to 20% by weight relative to the total weight of the composition and preferably ranging from 0.2% to 15% by weight relative to the total weight of the composition.

The cosmetic compositions in accordance with the invention can contain pigments or else nanopigments (mean size of the primary particles: generally between 5 nm and 100 nm and preferably between 10 nm and 50 nm) of coated or uncoated metal oxides, for instance titanium oxide (amorphous or crystallized in rutile and/or anatase form), iron oxide, zinc oxide, zirconium oxide or cerium oxide nanopigments, which are all UV-photoprotective agents that are well known per se. Alumina and/or aluminum stearate are also standard coating agents. Such coated or uncoated metal oxide nanopigments are described in particular in EP-A-0-518,772 and EP-A-0-518,773.

The compositions according to the invention may also contain agents for artificially tanning and/or browning the skin (self-tanning agents), for instance dihydroxyacetone (DHA).

The compositions of the present invention may also comprise standard cosmetic adjuvants chosen especially from fatty substances, organic solvents, ionic or nonionic thickeners, softeners, antioxidants, free-radical scavengers, opacifiers, stabilizers, emollients, silicones, $\alpha$-hydroxy acids, antifoams, moisturizers, vitamins, insect repellents, fragrances, preservatives, surfactants, anti-inflammatories, substance P antagonists, fillers, photoprotective agents, polymers other than those of the invention, propellants, acidifying or basifying agents, colorants or any other ingredient usually used in cosmetics or dermatology, in particular for the manufacture of self-tanning compositions in the form of emulsions.

The fatty substances may consist of an oil or a wax or mixtures thereof. The term "oil" means a compound that is liquid at room temperature. The term "wax" means a compound that is solid or substantially solid at room temperature, and whose melting point is generally greater than 35° C.

Oils that may be mentioned include mineral oils (paraffin); plant oils (sweet almond oil, macadamia oil, blackcurrent pip oil or jojoba oil); synthetic oils, for instance perhydrosqualene, fatty alcohols, fatty acids or fatty esters (for instance the $C_{12}$–$C_{15}$ alkylbenzoate sold under the trademark "Finsolv TN" by Finetex, octyl palmitate, isopropyl lanolate, and triglycerides, including capric/caprylic acid triglycerides), oxyethylenated or oxypropylenated fatty esters and ethers; silicone oils (cyclomethicone or polydimethylsiloxanes, or PDMS) or fluoro oils, and polyalkylenes.

Waxy compounds that may be mentioned include paraffin, carnauba wax, beeswax and hydrogenated castor oil.

Among the organic solvents that may be mentioned are lower alcohols and polyols.

The thickeners may be chosen in particular from crosslinked polyacrylic acids, modified or unmodified guar gums and celluloses such as hydroxypropyl guar gum, methylhydroxyethyl cellulose and hydroxypropylmethyl cellulose.

Needless to say, a person skilled in the art will take care to select this or these optional additional compound(s) and/or the amounts thereof such that the advantageous properties intrinsically linked to the compositions in accordance with the invention are not, or not substantially, adversely affected by the envisaged addition(s).

The compositions of the invention may be prepared according to techniques that are well known to those skilled in the art, in particular those intended for preparing emulsions of oil-in-water or water-in-oil type.

These compositions may be in particular in the form of a simple or complex emulsion (O/W, W/O, O/W/O or W/O/W emulsion) such as a cream, a milk, a gel or a cream-gel, of a powder, of a solid tube, and may optionally be packaged as an aerosol and be in the form of a mousse or a spray.

When it is an emulsion, the aqueous phase of this emulsion may comprise a nonionic vesicular dispersion prepared according to known processes (Bangham, Standish and Watkins, *J. Mol. Biol.* 13, 238 (1965), FR-2,315,991 and FR-2,416,008).

The cosmetic composition of the invention may be used as a composition for protecting the human epidermis or the hair against ultraviolet rays, as an antisun composition or as a makeup product.

When the cosmetic composition according to the invention is used for protecting the human epidermis against UV rays, or as an antisun composition, it may be in the form of a suspension or a dispersion in solvents or fatty substances, in the form of a nonionic vesicular dispersion or in the form of an emulsion, preferably of oil-in-water type, such as a cream or a milk, or in the form of an ointment, a gel, a cream-gel, a solid tube, a powder, a stick, an aerosol mousse or a spray.

When the cosmetic composition according to the invention is used for protecting the hair against UV rays, it may be in the form of a shampoo, a lotion, a gel, an emulsion or a nonionic vesicular dispersion and may constitute, for example, a rinse-out composition, to be applied before or after shampooing, before or after dyeing or bleaching, before, during or after permanent-waving or straightening the hair, a styling or treating lotion or gel, a blow-drying or hairsetting lotion or gel, or a composition for permanent-waving, straightening, dyeing or bleaching the hair.

When the composition is used as a makeup product for the eyelashes, the eyebrows or the skin, such as an epidermal treatment cream, a foundation, a tube of lipstick, an eyeshadow, a face powder, a mascara or an eyeliner, it may be in solid or pasty, anhydrous or aqueous form, for instance oil-in-water or water-in-oil emulsions, nonionic vesicular dispersions or suspensions.

As a guide, for the antisun formulations in accordance with the invention, which contain a support of oil-in-water emulsion type, the aqueous phase (comprising especially hydrophilic screening agents) generally represents from 50% to 95% by weight and preferably from 70% to 90% by weight, relative to the total formulation, the oily phase (comprising especially lipophilic screening agents) represents from 5% to 50% by weight and preferably from 10% to 30% by weight, relative to the total formulation.

AM signifies active material.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

The cosmetic compositions below, in accordance with the invention, are prepared:

Example 1

Shampoo

| | |
|---|---|
| Sodium lauryl ether sulfate sold under the name Empicol ESB3/FL by Albright & Wilson | 12 g AM |
| Benzophenone-1 | 0.5 g |
| Polymer P1 as defined in the description | 1 g AM |
| Citric acid | 3 g |
| Water pH adjusted to 4.8 (NaOH) | qs 100 g |

This shampoo has the appearance of a thickened translucent liquid and gives excellent performance qualities in terms of antisun protection.

Example 2

Styling Gel

| | |
|---|---|
| Vinylpyrrolidone/dimethylaminoethyl methacrylate copolymer sold under the name Copolymer 845 by ISP | 1 g AM |
| Benzophenone-4 | 1 g AM |
| Polymer P2 prepared as indicated in the description | 0.5 g AM |
| 2-Amino-2-methyl-1-propanol (AMP) pH adjusted to | 7.5 qs |
| Absolute ethanol | 8.7 g |
| Fragrance, preserving agent, colorant | qs |
| Demineralized water | qs 100 g |

A stable, thick, transparent, creamy and uniform gel is obtained. It gives excellent performance qualities in terms of antisun protection.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A photoprotective cosmetic/dermatological composition suited for the UV-photoprotection of the skin and/or hair, comprising (a) at least one organic UV-screening agent and (b) an SPF-improving amount of at least one amphiphilic polymerizate of at least one ethylenically unsaturated monomer which comprises a sulfonic group, whether in the free acid or in partially or totally neutralized state, and which amphiphilic polymerizate also comprises at least one hydrophobic moiety.

2. The cosmetic/dermatological composition as defined by claim 1, said at least one hydrophobic moiety of said at least one amphiphilic polymerizate having from 6 to 50 carbon atoms.

3. The cosmetic/dermatological composition as defined by claim 2, said at least one hydrophobic moiety of said at least one amphiphilic polymerizate having from 6 to 22 carbon atoms.

4. The cosmetic/dermatological composition as defined by claim 3, said at least one hydrophobic moiety of said at least one amphiphilic polymerizate having from 6 to 18 carbon atoms.

5. The cosmetic/dermatological composition as defined by claim 4, said at least one hydrophobic moiety of said at least one amphiphilic polymerizate having from 12 to 18 carbon atoms.

6. The cosmetic/dermatological composition as defined by claim 1, the sulfonic groups of said at least one amphiphilic polymerizate being partially or totally neutralized with a mineral or organic base.

7. The cosmetic/dermatological composition as defined by claim 1, said at least one amphiphilic polymerizate having a number-average molecular weight ranging from 1,000 to 20,000,000 g/mol.

8. The cosmetic/dermatological composition as defined by claim 7, said number-average molecular weight ranging from 20,000 to 5,000,000 g/mol.

9. The cosmetic/dermatological composition as defined by claim 8, said number-average molecular weight ranging from 100,000 to 1,500,000 g/mol.

10. The cosmetic/dermatological composition as defined by claim 1, an aqueous 1% by weight solution of said at least one amphiphic polymerizate having, at a temperature of 25° C., a viscosity, measured using a Brookfield viscometer with a No. 7 needle, ranging from 20,000 mPa·s to 100,000 mPa·s.

11. The cosmetic/dermatological composition as defined by claim 1, said at least one amphiphilic polymerizate having been prepared by free-radical precipitation polymerization in tert-butanol.

12. The cosmetic/dermatological composition as defined by claim 1, said at least one amphiphilic polymerizate being non-crosslinked.

13. The cosmetic/dermatological composition as defined by claim 1, said at least one amphiphilic polymerizate being crosslinked.

14. The cosmetic/dermatological composition as defined by claim 13, said at least one amphiphilic polymerizate being crosslinked with a polyolefinically unsaturated crosslinking agent.

15. The cosmetic/dermatological composition as defined by claim 14, said crosslinking agent comprising methylenebisacrylamide, allyl methacrylate or trimethylolpropane triacrylate (TMPTA).

16. The cosmetic/dermatological composition as defined by claim 14, the degree of crosslinking ranging from 0.01 mol % to 10 mol %.

17. The cosmetic/dermatological composition as defined by claim 1, said at least one ethylenically unsaturated monomer which comprises a sulfonic group comprising vinylsulfonic acid, styrenesulfonic acid, a (meth)acrylamido ($C_1$–$C_{22}$)alkylsulfonic acid, an N-($C_1$–$C_{22}$)alkyl(meth) acrylamido-($C_1$–$C_{22}$)alkylusulfonic acid, or the partially or totally neutralized forms thereof.

18. The cosmetic/dermatological composition as defined by claim 17, said at least one ethylenically unsaturated monomer which comprises a sulfonic group comprising acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2,6-di-methyl-3-heptanesulfonic acid, or the partially or totally neutralized forms thereof.

19. The cosmetic/dermatological composition as defined by claim 18, said at least one ethylenically unsaturated monomer which comprises a sulfonic group comprising 2-acrylamido-2-methylpropanesulfonic acid (AMPS), or the partially or totally neutralized forms thereof.

20. The cosmetic/dermatological composition as defined by claim 19, said at least one amphiphilic polymerizate comprising a random AMPS polymer modified by reaction with an n-mono($C_6$–$C_{22}$)alkylamine or a di-n-($C_6$–$C_{22}$)-alkylamine.

21. The cosmetic/dermatological composition as defined by claim 19, said amphiphilic AMPS polymerizate also being derived from at least one ethylenically unsaturated monomer not comprising a fatty chain.

22. The cosmetic/dermatological composition as defined by claim 20, said at least one ethylenically unsaturated monomer not comprising a fatty chain being selected from among (meth)acrylic acids and the β-substituted alkyl derivatives thereof, and the esters thereof obtained with monoalcohols or mono- or polyalkylene glycols, or from (meth)acrylamides, vinylpyrrolidone, maleic anhydride, itaconic acid or maleic acid, or mixtures thereof.

23. The cosmetic/dermatological composition as defined by claim 19, said amphiphilic AMPS polymerizate comprising an amphiphilic copolymer of AMPS and of at least one ethylenically unsaturated hydrophobic monomer which comprises at least one hydrophobic moiety having from 6 to 50 carbon atoms.

24. The cosmetic/dermatological composition as defined by claim 23, said at least one hydrophobic moiety having from 6 to 22 carbon atoms.

25. The cosmetic/dermatological composition as defined by claim 24, said at least one hydrophobic moiety having from 6 to 18 carbon atoms.

26. The cosmetic/dermatological composition as defined by claim 25, said at least one hydrophobic moiety having from 12 to 18 carbon atoms.

27. The cosmetic/dermatological composition as defined by claim 23, said at least one ethylenically unsaturated hydrophobic monomer comprising an acrylate or acrylamide of formula (I) below:

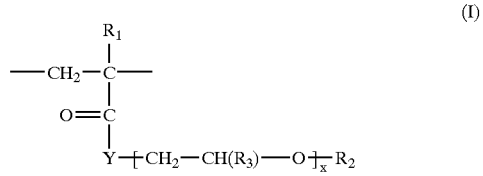

in which $R_1$ and $R_3$, which may be identical or different, are each a hydrogen atom or a linear or branched $C_1$–$C_6$ alkyl radical; Y is O or NH; $R_2$ is a hydrophobic hydrocarbyl radical having from 6 to 50 carbon atoms; and $\underline{x}$ is the number of moles of alkylene oxide and ranges from 0 to 100.

28. The cosmetic/dermatological composition as defined by claim 27, wherein formula (I) said hydrophobic radical $R_2$ is a linear, branched or cyclic $C_6$–$C_{18}$ alkyl radical; $C_6$–$C_{18}$ alkylperfluoro radical; cholesteryl radical or a cholesterol ester; or an aromatic polycyclic radical.

29. The cosmetic/dermatological composition as defined by claim 27, said at least one monomer of formula (I) comprising at least one alkylene oxide structural unit ($x \geq 1$).

30. The cosmetic/dermatological composition as defined by claim 27, said at least one monomer of formula (I) comprising at least one polyoxyalkylenated structural unit.

31. The cosmetic/dermatological composition as defined by claim 30, said at least one polyoxyalkylenated structural unit comprising ethylene oxide groups and/or of propylene oxide groups.

32. The cosmetic/dermatological composition as defined by claim 31, said at least one polyoxyalkylenated structural unit solely comprising ethylene oxide groups.

33. The cosmetic/dermatological composition as defined by claim 27, wherein formula (I) the number of oxyalkylenated structural units ranges from 3 to 100.

34. The cosmetic/dermatological composition as defined by claim 33, wherein formula (I) the number of oxyalkylenated structural units ranges from 3 to 50.

35. The cosmetic/dermatological composition as defined by claim 34, wherein formula (I) the number of oxyalkylenated structural units ranges from 7 to 25.

36. The cosmetic/dermatological composition as defined by claim 23, said at least one amphiphilic AMPS polymer comprising a crosslinked or non-crosslinked, neutralized or non-neutralized copolymer which comprises from 15% to 60% by weight of AMPS structural units and from 40% to 85% by weight of ($C_8$–$C_{16}$)alkyl(meth)acrylamide structural units or of ($C_8$–$C_{16}$)alkyl (meth)acrylate structural units, relative to the polymer; or a terpolymer which comprises from 10 mol % to 90 mol % of acrylamide structural units, from 0.1 mol % to 10 mol % of AMPS structural units and from 5 mol % to 80 mol % of n-($C_6$–$C_{18}$)alkyl-acrylamide structural units, relative to the polymer.

37. The cosmetic/dermatological composition as defined by claim 23, said at least one amphiphilic AMPS polymer comprising a non-crosslinked copolymer of partially or totally neutralized AMPS and of n-dodecyl methacrylate, or a crosslinked or non-crosslinked copolymer of partially or totally neutralized AMPS and of n-dodecyl-methacrylamide.

38. The cosmetic/dermatological composition as defined by claim 23, said at least one amphiphilic AMPS polymer comprising a copolymer of 2-acrylamido-2-methylpropanesulfonic acid (AMPS) structural units of formula (II) below:

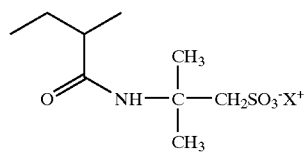

in which $X^+$ is a proton, an alkali metal cation, an alkaline earth metal cation or the ammonium ion, and of structural units of formula (III) below:

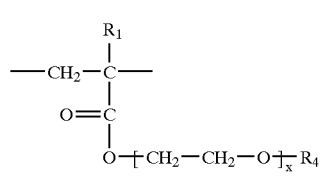

in which $\underline{x}$ is an integer ranging from 3 to 100, $R_1$ is as defined in formula (I); and $R_4$ is a linear or branched $C_6$–$C_{22}$ alkyl radical.

39. The cosmetic/dermatological composition as defined by claim 38, wherein formula (III) $\underline{x}=25$, $R_1$ is methyl and $R_4$ is n-dodecyl.

40. The cosmetic/dermatological composition as defined by claim 38, the molar percentage of structural units of formula (I) or of structural units of formula (III) in the polymer ranging from 50.1% to 99.9%.

41. The cosmetic/dermatological composition as defined by claim 38, the molar percentage of structural units of formula (I) or of structural units of formula (III) in the polymer ranging from 0.1% to 50%.

42. The cosmetic/dermatological composition as defined by claim 1, said at least one amphiphilic polymerizate comprising from 0.01% to 30% by weight thereof.

43. The cosmetic/dermatological composition as defined by claim 1, said at least one organic UV-screening agent being selected from among anthranilates; cinnamic derivatives; dibenzoylmethane derivatives; salicylic derivatives; camphor derivatives; triazine derivatives; benzophenone derivatives; β,β'-diphenylacrylate derivatives; benzotriazole derivatives; benzalmalonate derivatives; benzimidazole derivatives; imidazolines; bis-benzazolyl derivatives; p-aminobenzoic acid (PABA) derivatives; methylenebis(hydroxyphenylbenzotriazole) derivatives; screening polymers and screening silicones; dimers derived from α-alkylstyrene; and mixtures thereof.

44. The cosmetic/dermatological composition as defined by claim 43, said at least one organic UV-screening agent being selected from among the following compounds:
PABA,
Ethyl PABA,
Ethyl Dihydroxypropyl PABA
Ethylhexyl Dimethyl PABA
Glyceryl PABA,
PEG-25 PABA,
Homosalate,
Ethylhexyl Salicylate
Dipropyleneglycol Salicylate,
TEA Salicylate,
Butylmethoxydibenzoylmethane,
Isopropyldibenzoylmethane,
Ethylhexyl Methoxycinnamate,
Isopropyl Methoxycinnamate,
Isoamyl Methoxycinnamate,
Cinoxate,
DEA Methoxycinnamate,
Diisopropyl Methylcinnamate,
Glyceryl Ethylhexanoate Dimethoxycinnamate,
Octocrylene,
Etocrylene,
Benzophenone-1,
Benzophenone-2,
Benzophenone-3,
Benzophenone-4,
Benzophenone-5,
Benzophenone-6,
Benzophenone-8,
Benzophenone-9,
Benzophenone-12,
3-Benzylidenecamphor,
4-Methylbenzylidenecamphor,
Benzylidenecamphorsulfonic Acid,
Benzalkonium Camphor,
Terephthalidenedicamphorsulfonic,
Polyacrylamidomethylbenzylidenecamphor,
Phenylbenzimidazolesulfonic Acid,
Benzimidazilate,
Anisotriazine,
Ethylhexyl Triazone,
Diethylhexyl Butamido Triazone,
Drometrizole Trisiloxane,
Methylene bis-Benzotriazolyl Tetramethylbutyl-phenol,
Menthyl anthranilate,
Ethylhexyl Dimethoxybenzylidene Dioxoimidazoline Propionate,
Polyorganosiloxane containing benzalmalonate functions and mixtures thereof.

45. The cosmetic/dermatological composition as defined by claim 44, said at least one organic UV-screening agent being selected from among the following compounds:
ethylhexyl salicylate,
butylmethoxydibenzoylmethane,
ethylhexyl methoxycinnamate,
octocrylene,
phenylbenzimidazolesulfonic acid,
terephthalylidenedicamphorsulfonic,
benzophenone-3,
benzophenone-4,
benzophenone-5,
4-methylbenzylidenecamphor,
benzimidazilate,
anisotriazine,
ethylhexyltriazone,
diethylhexylbutamidotriazone,
methylenebis(benzotriazolyl)tetramethylbutylphenol,
drometrizole trisiloxane, and mixtures thereof.

46. The cosmetic/dermatological composition as defined by claim 1, said at least one organic UV-screening agent comprising from 0.1% to 20% by weight thereof.

47. The cosmetic/dermatological composition as defined by claim 1, further comprising coated or uncoated metal oxide pigments or nanopigments.

48. The cosmetic/dermatological composition as defined by claim 47, said pigments or nanopigments being selected from among titanium oxide, zinc oxide, iron oxide, zirconium oxide and cerium oxide, and mixtures thereof, whether coated or uncoated.

49. The cosmetic/dermatological composition as defined by claim 1, further comprising at least one active agent for artificially tanning and/or browning the skin.

50. The cosmetic/dermatological composition as defined by claim 1, further comprising at least one adjuvant selected from among fatty substances, organic solvents, ionic or nonionic thickeners, softeners, antioxidants, free-radical scavengers, opacifiers, stabilizers, emollients, silicones, α-hydroxy acids, antifoams, moisturizers, vitamins, insect repellents, fragrances, preservatives, surfactants, anti-inflammatories, substance P antagonists, fillers, polymers other than those of the invention, propellants, acidifying or basifying agents and colorants.

51. The cosmetic/dermatological composition as defined by claim 1, formulated as a nonionic vesicular dispersion, an emulsion, a cream, a milk, a gel, a cream-gel, a suspension, a dispersion, a powder, a solid tube, a mousse or a spray.

52. The cosmetic/dermatological composition as defined by claim 1, formulated as a makeup composition for the eyelashes, the eyebrows or the skin, in solid or pasty, anhydrous or aqueous form or in the form of an emulsion, a suspension or a dispersion.

53. The cosmetic/dermatological composition as defined by claim 1, formulated as a composition for protecting the hair against ultraviolet rays and in the form of a shampoo, a lotion, a gel, an emulsion or a nonionic vesicular dispersion.

54. A regime or regimen for photoprotecting the skin and/or hair against the damaging effects of UV-irradiation, comprising topically applying thereon a thus effective amount of a photoprotective cosmetic/dermatological composition, comprising (a) at least one organic UV-screening agent and (b) an SPF-improving amount of at least one amphiphilic polymerizate of at least one ethylenically unsaturated monomer which comprises a sulfonic group, whether in the free acid or in partially or totally neutralized state, and which amphiphilic polymerizate also comprises at least one hydrophobic moiety.

* * * * *